United States Patent [19]

Denning

[11] 4,165,743

[45] Aug. 28, 1979

[54] REGENERATED CELLULOSE FIBERS CONTAINING ALKALI METAL OR AMMONIUM SALT OF A COPOLYMER OF AN ALKYL VINYL ETHER AND ETHYLENE DICARBOXYLIC ACID OR ANHYDRIDE AND A PROCESS FOR MAKING THEM

[75] Inventor: David B. Denning, Asheville, N.C.

[73] Assignee: Akzona Incorporated, Asheville, N.C.

[21] Appl. No.: 745,934

[22] Filed: Nov. 29, 1976

[51] Int. Cl.$^2$ .............................................. A61F 13/18
[52] U.S. Cl. ................................ 128/290 R; 128/296; 260/17.4 CL; 264/191
[58] Field of Search ................ 8/74; 264/17, 17.4 CL, 264/188, 191, 194; 260/17 R; 128/284, 265, 290 R, 296

[56] References Cited

U.S. PATENT DOCUMENTS

| | | | |
|---|---|---|---|
| 2,142,007 | 12/1938 | Schlack | 264/78 |
| 2,267,842 | 12/1941 | Schlack | 264/78 |
| 2,686,103 | 8/1954 | Church | 264/191 |
| 2,880,051 | 3/1959 | Rosen et al. | 8/74 |
| 3,359,224 | 12/1967 | Laessinger et al. | 264/188 |
| 3,377,301 | 4/1968 | Williams et al. | 260/17 R |
| 3,509,249 | 4/1970 | Kuzmak et al. | 264/188 |
| 3,669,103 | 6/1972 | Harper et al. | 128/284 |
| 3,810,468 | 5/1974 | Harper et al. | 128/284 |
| 3,900,378 | 8/1975 | Yen et al. | 128/284 |
| 3,983,095 | 9/1976 | Bashow et al. | 128/284 |

FOREIGN PATENT DOCUMENTS 37-12014  8/1962  Japan ....................................... 264/188

*Primary Examiner*—Jay H. Woo
*Attorney, Agent, or Firm*—Francis W. Young; Jack H. Hall; Clelle W. Upchurch

[57] ABSTRACT

An alloyed regenerated cellulose fiber containing an alkali metal or ammonium salt of a copolymer of an alkyl vinyl ether and an ethylene dicarboxylic acid or anhydride is prepared by a process wherein the copolymer is mixed with a viscose solution and the mixture is spun through a spinneret into a suitable spin bath and processed into staple fibers adapted to be used in nonwoven absorbent articles such as diapers, tampons, sanitary napkins, wiping cloths and the like. The alloyed regenerated cellulose fiber of the invention has increased fluid absorbency characteristics over fibers of the same regenerated cellulose composition without the alloying material.

9 Claims, No Drawings

REGENERATED CELLULOSE FIBERS CONTAINING ALKALI METAL OR AMMONIUM SALT OF A COPOLYMER OF AN ALKYL VINYL ETHER AND ETHYLENE DICARBOXYLIC ACID OR ANHYDRIDE AND A PROCESS FOR MAKING THEM

This invention relates generally to absorbent cellulosic fibers, for example, viscose rayon, hydroxypropyl cellulose and hydroxyethyl cellulose made from wood pulp or other cellulosic material, and particularly to a regenerated cellulose fiber having improved water and body fluid absorbency and to a process for preparing the fiber.

In accordance with the conventional viscose process, chemical cellulose from wood pulp or cotton linters is converted into regenerated cellulose by a series of steps in which the cellulose is first treated with a sodium hydroxide solution to mercerize it and to form alkali cellulose. The alkali cellulose, after aging, is reacted with carbon disulfide to form a soluble sodium xanthate derivative. The xanthate cellulose is later dissolved in dilute aqueous sodium hydroxide to form viscose which, after ripening, is spun by extrusion through a spinneret into a spin bath containing sulfuric acid and various metal salts which coagulates the strands of viscose solution into individual filaments of regenerated cellulose. These filaments may be collected as a cake of a mass of filaments or processed into a tow and cut into staple fibers.

Staple fibers prepared by the viscose process are used extensively in making articles which are used to absorb water and body fluids such as, for example, surgical bandages, diapers, sanitary napkins, tampons and the like.

It has been proposed before to improve the absorbency of staple fibers of regenerated cellulose by alloying the regenerated cellulose with another material. For example, in accordance with the disclosure in U.S. Pat. No. 3,844,287 an alkali metal or ammonium salt of polyacrylic acid is mixed with the viscose solution before the solution is extruded to improve the absorbency characteristics of the fiber. In accordance with the disclosed process, a caustic solution of polyacrylic acid is mixed with viscose and the mixture is spun into a suitable coagulating bath to form fibers which are purified and dried with an alkaline lubricating finish thereon. Such staple alloy fibers are known to be more absorbent and to have improved fluid retention properties over the non-alloyed regenerated cellulose fibers.

It is proposed in U.S. Pat. No. 2,880,051 to improve the gas fading resistance of textile materials made from cellulose acetate, cellulose propionate, cellulose butyrate, cellulose acetate propionate, cellulose acetate butyrate, ethyl cellulose, benzyl cellulose and polyethylene terephthalate by incorporating in the textile an alkaline salt of a copolymer of an alkyl vinyl ether and an ethylene dicarboxylic acid. It is disclosed that the product has a reduced tendency to change shade or color when exposed to acid fumes.

It is an object of this invention to provide a process for making an alloy fiber of cellulosic materials which has improved fluid absorbency and improved fluid retention. Another object of the invention is to provide a process for making an alloy fiber of cellulosic materials and a copolymer which can be used to advantage in making articles for fluid absorbent applications. Still another object of the invention is to provide a fiber of regenerated cellulose having improved absorbency for water and body fluids adapted to be used in making articles for absorbing water and body fluids to be used in association with parts of the human body.

The foregoing objects and others are accomplished in accordance with this invention, generally speaking, by providing a process for making alkaline alloy cellulosic fibers wherein an alkali metal salt or ammonium salt of a copolymer of an alkyl vinyl ether and an ethylene dicarboxylic acid or anhydride is substantially uniformly mixed with a spinnable solution of a cellulosic material, the material is spun into a suitable spin bath and the resulting cellulosic fiber is processed into staple fiber adapted to be used in an article for absorbing water or body fluids. The invention contemplates broadly alloy cellulosic fibers including hydroxypropyl cellulose and hydroxyethyl cellulose but the preferred cellulose is viscose rayon. It has been found in accordance with this invention that the fluid absorbency and fluid retention of viscose rayon fibers containing the said copolymer is significantly greater than the fluid absorbency and retention of fibers made from the same viscose solution without the addition of the alloying copolymer. Although the invention in its broadest aspects contemplates any alkali metal or ammonium salt of alkyl vinyl ether-ethylene dicarboxylic acid or anhydride copolymer, a salt of a copolymer of methyl vinyl ether and maleic anhydride or maleic acid is preferred.

In practicing the invention, it has been found preferable to spin a suitable viscose solution containing sodium cellulose xanthate, sodium hydroxide and carbon disulfide mixed with a salt of the copolymer of an alkyl vinyl ether and an ethylene dicarboxylic acid, preferably an $\alpha, \beta$-unsaturated aliphatic dicarboxylic acid, into a spin bath containing sulfuric acid, sodium sulfate and/or magnesium sulfate and zinc sulfate of predetermined concentrations, rinse with water, stretch in air, finish, and dry as in conventional prior art processes. The viscose solution may be first prepared by conventional steps. This may include steeping conventional chemical cellulose sheet prepared from wood pulp or cotton linters in a caustic soda solution (NaOH) and thereafter removing caustic soda by pressing or the like to the desired solids content. The resulting alkali cellulose is shredded and, after aging, is mixed with carbon disulfide to form an aqueous alkaline xanthate (viscose) solution. For best results, the concentration of the viscose solution is from about 5 to about 10 percent by weight cellulose, from about 4 to about 9 percent by weight sodium hydroxide, from about 1.5 to about 3 percent sulfur and the remainder water.

The alkali metal or ammonium salt of the copolymer of the invention is mixed with the viscose solution at any stage during aging preferably in an amount of from about 2 to about 35 percent by weight copolymer based on the weight of cellulose in the solution. The copolymer can be neutralized with ammonium hydroxide or an alkali metal hydroxide such as sodium hydroxide, before it is added to the viscose solution. For example, the copolymer may be neutralized in an aqueous solution and added as the sodium salt in an aqueous sodium hydroxide solution to the viscose solution, preferably by injection into the viscose solution just before the viscose solution is extruded. Preferably, the copolymer has a molecular weight of 100,000 to 1,500,000.

In a preferred embodiment of the invention, the viscose solution containing the copolymer is spun or extruded through spinneret openings into an acid bath where the cellulose fiber is regenerated. The regenerated fiber is stretched in air from 0–100%, or even higher, if desired, preferably from about 30% to 50% and then run through a hot aqueous bath maintained at a temperature of from ambient to 100° C., preferably from 90°–97° C. The hot aqueous bath may contain any amount of dilute sulfuric acid, MgSo$_4$, ZnSO$_4$, and sodium sulfate depending upon the characteristics desired in the fiber. The fiber is subjected to a second stretching of from 0 to 100% in the hot bath. The total stretch in both steps is preferably in the range of 50–70%. The stretching, as is well known, imparts the necessary strength to the finished fiber. The fibers in the form of large bundles of continuous filaments or tow from the combined output of a number of spinnerets are cut into short fibers of any desired length and washed and dried to a moisture content of around 11% and baled.

After the fiber is regeneraged in the acid bath, the copolymer occluded in the fiber may be in acid form. As many of the acid groups of the copolymer should be in the form of an alkali metal salt in order to achieve the highest degree of absorbency. The copolymer may be converted into the salt form during the alkaline sodium sulfide wash of the fiber which is conventionally used to remove metal and sulfur impurities. In some instances, it may be desirable, particularly, if an acid wash follows the sulfide, to treat the fiber with a base such as a dilute solution of sodium bicarbonate, sodium hydroxide, or the like, to complete the conversion, and insure that a high percentage of the copolymer is in the salt form. It may be desirable to limit the amount of copolymer converted to the salt form for certain applications where the material may come into contact with the body, since a pH which is much higher than 7 to 7.5 can cause irritation of delicate membranes and serves to promote the growth of harmful microorganisms. Subsequently, a conventional finish, such as a surfactant, may be applied and the staple fibers may be dried in a suitable hot air drier to a predetermined moisture content suited to the particular end use of the fiber.

The fiber can then be baled or carded for processing into one of the final products mentioned previously. A particularly suitable use for the fiber of the invention is for tampons, which may be made, for example, by one of the methods referred to in U.S. Pat. No. 3,699,965, or by other well-known methods.

Any suitable ethylene dicarboxylic acid or anhydride may be used to prepare the copolymer such as, for example, maleic acid, fumaric acid, maleic anhydride, citraconic acid and anhydride, itaconic acid and anhydride, the mono-methyl, mono-ethyl or mono-propyl esters of maleic acid and the mono-methyl, mono-ethyl or mono-propyl esters of fumaric acid, and the like, or mixtures thereof but best results have been obtained so far with regenerated cellulose fibers containing a copolymer of maleic anhydride and methyl vinyl ether. However, any suitable alkyl vinyl ether may be used in the copolymer such as, methyl vinyl ether, ethyl vinyl ether, propyl vinyl ether, butyl vinyl ether, isobutyl vinyl ether, pentyl vinyl ether, hexyl vinyl ether, and the like. Preferably the alkyl group of the vinyl ether will have 1 to 6 carbon atoms.

The copolymers of the invention may be prepared by any suitable known process. The viscosity of the copolymer is an indication of the degree of polymerization and of the molecular weight of the copolymer. A copolymer having a higher molecular weight will generally be retained to a greater degree in the fiber than one of lower molecular weight, but if the copolymer is to be injected into the viscose, the molecular weight is limited by the viscosity which can be pumped. Pumping systems are generally available which can handle fluids at viscosities of 10,000 cps and over. Copolymers of a wide range of viscosities can be used if the copolymer is added to the dissolver.

The percent water retention as indicated by the secondary swelling of a rayon fiber may be determined by soaking 2 to 3 g. of previously washed and dried rayon fiber in water, and removing excess water by centrifuging at a force of 2500 to 3500 times gravity for 15 minutes in stainless steel sample holders. These holders are 22 mm. I.D.×25 mm. deep, with screw caps to cover both ends. Space is provided in the centrifuge cup below the sample holder to contain the excess water which is removed from the yarn during centrifuging. The extracted fiber is placed in a preweighed weighing bottle; the weight of the swollen fiber is obtained and, after drying overnight at 105° C., the weight of the dry fiber is determined. The percent swelling is then determined by use of the following equation:

$$Q = \frac{\text{Swollen weight} - \text{dry weight} \times 100}{\text{dry weight}}$$

U.S. Pat. No. 3,670,069, column 6, describes a method for making this determination. The secondary swelling is an indication of the fluid absorbency of the fiber, the larger the percentage, the greater the absorbency of the fiber.

In the following examples, all parts are by weight unless otherwise stated.

EXAMPLE I

In this Example a rayon fiber which does not contain any alloying polymer or copolymer was prepared and tested for comparison with fibers prepared in accordance with the invention.

A ripened viscose solution containing 8.4% cellulose, 4.85% sodium hydroxide, and 2.48% sulfur was extruded through a spinneret into a spinbath. The spinbath contained 8.5% sulfuric acid, 18.25% sodium sulfate, 5% magnesium sulfate and 3% zinc sulfate in water. The temperature of the spinbath was about 50° C. The resulting continuous filament yarns had a denier of 1100 and contained 480 filaments and was collected in a centrifugal pot in the form of a cake.

The cake of yarn was purified with the procedure of Table III and dried and cut in staple fiber lengths. After conditioning, water retention (secondary swelling) determinations were made on the staple fibers. The secondary swelling of the fiber was 67%.

EXAMPLE II

About 5%, based on the weight of the cellulose in the viscose solution of Example I, of a copolymer of methyl vinyl ether and maleic anhydride having a molecular weight of about 250,000 was injected into a portion of the viscose solution of Example I. The copolymer is available commercially under the trademark GANTREZ AW-119. The copolymer was neutralized with sodium hydroxide to a pH 7 before it was added to the viscose solution. After thorough mixing in an in-line mixer, the resulting viscose containing the copolymer was spun in a conventional manner into the spinbath described in Example I at a temperature of 50° C. The resulting cake of continuous filamentary fiber, having a denier of 1100 and containing 480 filaments, was washed and dried by the same procedure as used in Example I. After conditioning, water retention (secondary swelling) determinations were made on the fiber. The secondary swelling of the staple fiber was 111%.

EXAMPLES III–V

Example II was repeated except that the pH of the copolymer, the molecular weight of the copolymer and the percentage copolymer were varied as indicated in Table I which also includes the corresponding values of Examples I and II to facilitate comparison.

TABLE I

| Example No. | pH Copolymer | % Copolymer | MW of Copolymer | Secondary Swelling % |
|---|---|---|---|---|
| I | — | none | — | 67 |
| II | 7 | 5.0 | 250,000 | 111 |
| III | 1.8 | 5 | 250,000 | 111 |
| IV | 6.4 | 5 | 1,250,000 | 106 |
| V | 1.7 | 15 | 250,000 | 132 |

EXAMPLES VI–VIII

Example I was repeated as Example VI using a ripened viscose solution different from the one of Example I and containing 8.4% cellulose, 4.85% sodium hydroxide and 2.48% sulfur. The viscose solution did not contain any alloying polymer or copolymer. The viscose solution was extruded into a spin bath through a spinneret to form filaments having a denier of 1100 into a cake of 480 fibers. The aqueous spin bath contained 8.5% sulfuric acid, 18.2% sodium sulfate, 5% magnesium sulfate and 3% zinc sulfate. The fibers were washed with the series of steps listed in Table IV.

The procedure of Example II was repeated as Examples VII and VIII using the viscose solution and spin bath of Example VI for comparison. The details of Examples VI through VIII are recorded in Table II.

TABLE II

| Example No. | pH Copolymer | % Copolymer In Fiber | MW of Copolymer | Secondary Swelling % |
|---|---|---|---|---|
| VI | | none | | 91 |
| VII | 6.89 | 5 | 500,000 | 102 |
| VIII | 7.08 | 5 | 800,000 | 133 |

The copolymer of Example VII was a copolymer of methyl vinyl ether and maleic anhydride sold commercially as GANTREZ AN-139. The pH of the dried fiber was 8.62. The copolymer of Example VIII was a copolymer of methyl vinyl ether and maleic anhydride sold commercially as GANTREZ AN-149. The pH of the dried fiber in water was 8.85.

The fibers were washed and purified as set forth in Table IV.

TABLE III

| Step | Solutions and Sequence | Conc. % | Temp. °C. | Pressure Lbs. | Time Mins. |
|---|---|---|---|---|---|
| 1 | Soft Water (after 5 min., clean filter) | 5 ppm Max. H. | 25–35 | 9–10 | 105 |
| 2 | Sulfuric Acid | 0.15–0.25 | 25–35 | 9–10 | 35 |
| 3 | Soft Water | 5 ppm Max. H. | 25–35 | 9–10 | 35 |
| 4 | Desulfuring | Na$_2$S:0.45–0.55 NaOH:0.45–0.10 | 50–55 | 9–10 | 70 |
| 5 | Soft Water (after 5 min., clean filter) | 5 ppm Max. H. | 25–35 | 9–10 | 35 |
| 6 | Soda Bleach | NaOCl:0.18–0.20 | 25–35 | 9–10 | 70 |
| 7 | Soft Water | 5 ppm Max. H. | 25–35 | 9–10 | 35 |
| 8 | Sodium Thiosulfate | 0.12–0.15 | 25–35 | 9–10 | 35 |
| 9 | Soft Water | 5 ppm Max. H. | 25–35 | 9–10 | 35 |
| 10 | Hydrochloric Acid (Muriatic Acid) | 0.45–0.60 | 25–35 | 9–10 | 35 |
| 11 | Soft Water (after 5 min., clean filter) | 5 ppm Max. H. | 25–35 | 9–10 | 35 |
| 12 | Sodium Bicarbonate | 0.20–0.30 | 25–35 | 9–10 | 35 |
| 13 | Soft Water (after 5 min., clean filter) | 5 ppm Max. H. | 25–35 | 9–10 | 35 |
| 14 | Acetic Acid | 0.011–0.013 | 25–35 | 9–10 | 35 |
| 15 | NOPCO 1921-D* (finish) | 0.65–0.75 | 45–50 | 7–8 | 35 |

*74% mineral oil, 22% sulfonated butyl oleate, 4% water

TABLE IV

| Step | Solutions and Sequence | Conc. % | Temp. °C. | Pressure Lbs. | Time Mins. |
|---|---|---|---|---|---|
| 1 | Sulfuric Acid | 0.10–0.15 | 25–35 | 9–10 | 40 |
| 2 | Soft Water (after 5 min., clean filter) | 5 ppm Max. H. | 25–35 | 9–10 | 120 |
| 3 | Desulfuring Sodium Sulfide | Na$_2$S:0.45–0.55 NaOH:0.05–0.10 | 50–55 | 9–10 | 40 |
| 4 | Soft Water (after 5 min., clean filter) | 5 ppm Max. H. | 25–35 | 9–10 | 80 |
| 5 | Acetic Acid | 0.01 | 25–35 | 9–10 | 40 |
| 6 | NOPCO 1921-D (finish) | 0.2 | 35–45 | 9–10 | 40 |

It can be seen from the secondary swelling results in Tables I and II that the alloy regenerated cellulose fibers provided by this invention have improved water absorbency over fibers prepared from the same viscose solution which does not contain the copolymer of the invention. Because of the improved absorbency characteristics of the fibers of the invention, they can be cut to staple fiber lengths and used to advantage in the manufacture of articles to be used for absorbing water and body fluids such as, for example, wiping cloths, surgical bandages, diapers, tampons, sanitary napkins, and the like.

The copolymer mixed with the viscose solution may be neutralized or partially neutralized with any suitable alkali metal hydroxide or ammonium hydroxide but for practical reasons sodium hydroxide is preferred. The copolymer is preferably neutralized to a pH of about 7.

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. A fluid absorbent regenerated cellulose fiber containing in physical admixture therewith from about 2 to about 35% by weight based on the weight of the cellulose of a water-soluble alkali metal or ammonium salt of a copolymer of an alkyl vinyl ether and an unsaturated dicarboxylic acid or anhydride, having a molecular weight of at least about 250,000 said fibers being more absorbent than non-alloyed cellulosic fibers.

2. The fiber of claim 1 wherein the copolymer is an alkyl vinyl ether-ethylenic α,β-dicarboxylic acid or anhydride copolymer.

3. The fiber of claim 2 wherein the said acid is maleic acid.

4. The fiber of claim 2 wherein the copolymer is a copolymer of methyl vinyl ether and maleic anhydride.

5. An article of manufacture comprising a fluid absorbent mass of fibers comprising a physical mixture of cellulose and from about 2 to about 35% weight based on the weight of the cellulose of a water-soluble alkali metal salt of a copolymer of an alkyl vinyl ether and an unsaturated aliphatic dicarboxylic acid or anhydride.

6. The article of claim 5 wherein the copolymer is a copolymer of methyl vinyl ether and maleic anhydride.

7. The article of claim 5 as a pad adapted to be used for absorbing body fluids.

8. A method for improving the fluid absorbency of a regenerated cellulose fiber which comprises incorporating in a viscose solution a water-soluble alkali metal or ammonium salt of a copolymer of an alkyl vinyl ether and an unsaturated aliphatic dicarboxylic acid or anhydride in an amount of from about 2 to about 35% by weight, extruding the mixture into an acidic medium to regenerate the cellulose, and stretching, purifying and drying the resulting fiber containing a water soluble alkali metal or ammonium salt in physical admixture with said cellulose.

9. The method of claim 8 wherein the copolymer is a copolymer of methyl vinyl ether and maleic anhydride.

* * * * *